United States Patent [19]

Kumar

[11] Patent Number: 5,502,168
[45] Date of Patent: Mar. 26, 1996

[54] **MONOCLONAL ANTIBODIES TO A CONTINUOUS AND CROSS-REACTIVE EPITOPE AND AN ISOLATED PROTEIN OF A SEXUAL STAGE OF *P. FALCIPARUM***

[75] Inventor: Nirbhay Kumar, Bethesda, Md.

[73] Assignee: The Johns Hopkins University, Baltimore, Md.

[21] Appl. No.: 120,225

[22] Filed: Sep. 14, 1993

Related U.S. Application Data

[63] Continuation of Ser. No. 779,494, Oct. 24, 1991, abandoned.

[51] Int. Cl.$^6$ .................... A61K 35/16; C07K 16/00
[52] U.S. Cl. .................. 530/388.4; 530/387.1; 530/387.9; 530/388.1; 530/326; 530/350; 435/70.21; 435/172.2; 435/240.27
[58] Field of Search ............... 435/70.21, 172.2; 530/240.27, 388.4, 326, 350, 387.9, 387.1, 388.1

[56] References Cited

U.S. PATENT DOCUMENTS 4,632,909 12/1986 Carter et al. ..................... 436/542

OTHER PUBLICATIONS

Waldmann Science 252:1657–1662 (1991).
Harris et al. TIBTECH 11:42–46 (1993).
Osband et al. Immunotherapy 11(6):193–195 (1990).
Dillman Ann. Internal Med. 111:592–603 (1989).
Hird et al. Genes and Cancer, published 1990 by Wiley & Sons Ltd, chapter 17, ed. Carnet et al.
Webster's Ninth New Collegiate Dictionary p. 871 and 947 (1990).
Miller et al, Science, 234:1349–1356 (Dec. 12, 1986).
Good et al, Immunology Today, 9(11):351–355 (1988).
Carter et al, Prog. Allergy, 41:193–214 (1988).
Rener et al, J. Exp. Med., 158:976–981 (1983).
Quakyi et al, J. Immunol., 139:4213–4217 (1987).
Kaslow et al, Nature, 333:74–76 (1988).
Vermeulen et al, Mol. Biochem. Parasitol., 20:155–163 (1986).
Kumar et al, Mol. Biochem. Parasitol., 13:333–342 (1984).
Fries et al, Exp. Parasitol, 71:229–235 (1990).
Ifediba et al, Nature, 296:364–366 (1981).
Kumar, Biochem. Parasitol., 17:343–358 (1985).
Carter et al, Esp. Parasitol., 69:140–149 (1989).
Bruce et al, Parasitology, 100:191–200 (1990).
Walliker et al, Science, 236:1661–1666 (1987).
Graves et al, Parasite Immol., 10:209–218 (1988).
Kumar, Parasite Immol., 9:321–335 (1987).
Moelans et al, Mol. Biochem. Parasitol., 45:193–204 (1991).
Barr et al, Journal of Exp. Medicine, 174:1203–1208 (1991).
Carter et al, Parasite Immunology, 12:587–603 (1990).
Gwadz et al, Infection and Immunity, 44:137–140 (1984).
Good et al, Science, 242:574–577 (1988).
Alano et al, Annu. Rev. Microbiol., 44:429–449 (1990).
Alano, et al Molecular & Biochemical Parasitology 46:81–88 May 1991.
Perrin, et al Nature 269:301–303 Jan. 22, 1981.
Harlow, et al Antibodies A Laboratory Manual.

*Primary Examiner*—Donald E. Adams
*Attorney, Agent, or Firm*—Cushman, Darby & Cushman

[57] ABSTRACT

Monoclonal antibodies which recognize a continuous epitope in the sexual stages of *P. falciparum*. The epitope so recognized has the following amino acid sequence:

Met—Ser—Lys—Val—Gln—Lys—Asp—Ser—Ala—Lys—
Pro—Leu—Asp—Lys—Phe—Gly—Asn—Ile—Tyr—Asp

Malaria vaccines based on this epitope are also disclosed.

3 Claims, 8 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 20 amino acids
      ( B ) TYPE: amino acid
      ( D ) TOPOLOGY: linear ( x i ) SEQUENCE DESCRIPTION: SEQ ID NO:1:

Met  Ser  Lys  Val  Gln  Lys  Asp  Ser  Ala  Lys  Pro  Leu  Asp  Lys  Phe  Gly
   1                   5                        10                       15

Asn  Ile  Tyr  Asp
                  20

( 2 ) INFORMATION FOR SEQ ID NO:2:

( i ) SEQUENCE CHARACTERISTICS:
      ( A ) LENGTH: 39 base pairs
      ( B ) TYPE: nucleic acid
      ( C ) STRANDEDNESS: double
      ( D ) TOPOLOGY: linear ( x i ) SEQUENCE DESCRIPTION: SEQ ID NO:2:

GATCATATGT TAACAGATAT CAAGGCCTGA CTGACTGAG                                     39

MONOCLONAL ANTIBODIES TO A CONTINUOUS AND CROSS-REACTIVE EPITOPE AND AN ISOLATED PROTEIN OF A SEXUAL STAGE OF P. FALCIPARUM

The invention described and claimed herein was made under Grant No. R29AI24704 from the National Institutes of Health.

This is a continuation of patent application Ser. No. 07/779,494, filed on Oct. 24, 1991, now abandoned.

The present invention relates to malaria vaccines, to a continuous (or reduction-insensitive), cross-reacting and conserved epitope in Plasmodium falciparum (designated as $C^3$-epitope) useful for such vaccines and to monoclonal antibodies which recognize such an epitope.

BACKGROUND OF THE INVENTION

Malaria remains a major public health problem in the world with nearly half the world's population living in malaria endemic areas. It is estimated that there are some 500 million new infections every year with 2–3 million deaths, especially of young children, annually.

The development of malaria vaccines remains a highly desirable goal as Plasmodium falciparum, which is responsible for malaria and its transmission, continues to become resistant to new generation anti-malaria drugs. Extensive research efforts are underway to find a vaccine which is effective but so far these efforts have been to no avail. Various targets for current vaccine efforts include the infective sporozoites, erythrocytic asexual stages and the sexual stages which are responsible for transmission of malaria. Some of the stumbling blocks in this as-yet unattained goal are antigenic variation and polymorphism of both T and B cell epitopes, and the predominantly conformational nature of the epitopes in the target antigens (1,2). Most antigens identified thus far as the targets for immunity directed against the parasite stages found in the mosquito vector are in fact conformational, and this makes the development of an effective vaccine particularly difficult. This form of immunity, which is also known as transmission-blocking immunity (TBI), is largely antibody mediated and operates in the mosquito midgut to block either fertilization of female gametes by the male gametes or results in the interruption of subsequent development of zygotes (3). Target antigens of TBI have been defined using monoclonal antibodies (MAbs). They include a set of three gamete surface proteins of apparent Mr 230, 48 and 45 kDa identified by fertilization blocking antibodies (4–6), and a single protein of 25 kDa present in the surface of zygotes/ookinetes, recognized by post-fertilization blocking antibodies (7–9). The gamete surface antigens are produced by the blood-stage gametocytes and the 25 kDa protein predominantly after initiation of gametogenesis and fertilization in the mosquito midgut (10–12).

In almost every case, the epitopes recognized by transmission blocking MAbs have been found to be reduction-sensitive, hence conformational in nature (3). It is believed that the conformational nature of the epitopes recognized by transmission blocking antibodies largely accounts for the fact that such antibodies have not proven useful in cloning the genes from prokaryotic expression libraries. Nevertheless, even if genes are cloned using other approaches e.g., by means of oligonucleotides based on protein microsequence data, reproducing such conformational epitopes in the recombinant expression systems would be difficult, if not impossible.

On the other hand, the identification of reduction-insensitive continuous epitopes of blocking antibodies would greatly facilitate development of a recombinant or peptide-based subunit vaccine. The relevant peptide epitopes can be chemically defined and synthesized or expressed, to develop a subunit vaccine. The vaccine can also be designed by the addition of appropriate helper T lymphocyte epitopes (which are also comprised of a linear stretch of 7–15 amino acids) or the equivalent, to stimulate the appropriate immune response.

BRIEF DESCRIPTION OF THE INVENTION

The invention includes the identification and expression in bacterial systems of continuous epitopes of malaria transmission-blocking immunity.

Identification of continuous epitopes in the target antigens of Plasmodium falciparum transmission blocking antibodies enable the production of a subunit vaccine. Using murine monoclonal antibodies, two such epitopes shared among several antigens specific to sexual stages of P. falciparum have been identified. One such epitope ($C^3$-epitope), recognized by four monoclonal antibodies capable of blocking infectivity of gametocytes in the mosquitoes, is shared among three antigens (apparent Mr 230, 48/45 doublet and 27 kDa). These antigens are synthesized at different time points during the development and maturation of gametocytes in the infected host. Furthermore, the blocking epitope appears to be conserved among parasites from diverse geographical locations. Both of these features are important for vaccine purposes. Studies have also shown that this epitope is a target of immune response during natural infection. Hence immune response against such novel epitope in P. falciparum gametocyte antigens (continuous, cross-reacting and conserved) is likely to be boosted by natural infection. All of these features make the $C^3$-epitope an attractive candidate for the development of a malaria transmission blocking vaccine.

Transmission-blocking monoclonal antibodies described above identified the recombinant expressed product of the cloned gene for the 27 kDa antigen gene. The entire coding sequence has been obtained using polymerase chain reaction and inserted in the expression plasmid pMG1. Two overlapping fragments spanning the 27 kDa antigen (designated as F1 and F2), produced with the help of polymerase chain reaction, have been expressed and the epitope has been mapped to the fragment F1. Subfragments of F1 (designated as F1a and F1b) were likewise produced using polymerase chain reaction cloning and expression, and the epitope has been mapped to the F1a subfragment (56 amino acids long). This epitope has been identified by using synthetic peptides which are 20 amino acids long.

Sexual reproduction of malaria parasites in the mosquito midgut is responsible for continued transmission of malaria from one infected host to another host. It is also during fertilization of malarial gametes that genetic recombination occurs possibly leading to selection of the variants capable of survival in the immunocompetent human host. It is therefore highly desirable to hinder the processes that are responsible for procreation of such variants occurring naturally as well as mutants arising due to immune and/or drug pressure. The results described herein support the development of a subunit vaccine against sexual stages. Identification of a novel continuous epitope shared among known major target antigens of TBI and a highly abundant 27 kDa protein in the sexual stages of the parasite is believed to provide an ideal target for antibody-mediated immunity. Antigens exhibiting this cross-reactivity appear as early as at the time of sexual differentiation of parasites during schizogony in the vertebrate host and are present during further maturation of gametocytes in the host. Analysis of immune human sera has revealed that the three gamete surface proteins (Mr 30, 48, 45 kDa) and the 27 kDa protein which are all synthesized in the gametocyte, are targets of immune response during natural infection. This is in contrast to the 25 kDa zygote/ookinete protein, which is produced and present predominantly in the mosquito midgut stages, and is not a natural target of immune response during infection. Thus an immune response against the $C^3$-epitope, which is shared among several antigens in vertebrate stages of the parasite, has the advantage of possible boosting during natural infection.

As indicated, the invention is based on the identification of a continuous, cross-reacting and conserved epitope in the malaria parasite. This identification is accomplished by means of *Plasmodium falciparum* transmission-blocking monoclonal antibodies. This identification makes possible the chemical synthesis or expression of the epitope to provide a vaccine for use against human malaria and its transmission.

The thus identified epitope ($C^3$-epitope) may be more fully described as the continuous epitope shared among the gamete surface proteins of 230 and 48/45 kDa and a protein of 27 kDa produced in the early stages of gametocytes and present also in the mature stages of gametocytes. The epitope is identified by monoclonal antibodies which recognize the thus shared linear epitope. These monoclonal antibodies are identified herein as MAbs 6B6, 16C3, 19F1, and 11G12.

The monoclonal antibodies are obtained in conventional fashion using the Milstein procedure as described hereinafter.

The terms "continuous", "cross-reacting" and "conserved" as used herein may be defined as follows:

"continuous" means reduction-insensitive (non-conformational);

"cross-reacting" means presence in more than one antigen; and

"conserved" means presence in many diverse geographical isolates of parasites.

BRIEF DESCRIPTION OF THE DRAWINGS

FIGS. 1–9 illustrate various aspects of the invention. More particularly.

DETAILED DESCRIPTION OF THE INVENTION

The following protocols and experimental details are referenced in the Examples given hereinafter.

Parasites

*Plasmodium falciparum* gametocytes were obtained in vitro as described (13). Parasites [isolate NF54 (Amsterdam Airport strain), LE5 (Liberian clone), 3D7 (a clone derived from NF54), 7G8 and ItD12 (clones of Brazilian isolates IMTM 22 and Ituxi respectively)], and T4 (a clone of Thai isolate)] were obtained from the Malaria section, Laboratory of Parasitic Disease, NIAID-NIH, Bethesda, Md., and CVD-1 (another clone of NF54) from the University of Maryland, Baltimore, Md. Female gametes and zygotes were purified by 'Nycodenz' discontinuous gradient centrifugation (5,6), after induction of gametogenesis.

Production of Monoclonal Antibodies

Balb/cJ and CAF1/J (F1 hybrid of Balb/cJ and A/J) mice were immunized i.p. with 3D7 gametes in complete Freund's adjuvant and boosted three times at 30 days interval in incomplete Freund's adjuvant. The number of gametes varied between $5 \times 10^6$ and $1 \times 10^7$ for the primary immunization and $5 \times 10^6$ and $7 \times 10^6$ for the booster immunizations in all the 10 fusions. Mice received a final booster in PBS given i.v. four days prior to fusion. Mice tail bleeds were tested by indirect immunofluorescence assay (IFA) and immunoprecipitation for antibodies.

Spleen cells were fused with myeloma cells P3-X63-Ag8.653 (ATCC CRL 1580). Hybrid cells were grown in two to six, 24-well plates using HAT-selective DMEM supplemented with 10% NCTC-109, 10% EL-4 (ATCC TIB 39) spent medium, 1% non-essential amino acids, and 10% FCS. Culture supernatants, 10 to 14 days after fusion, were screened for antibodies by IFA using methanol-fixed gametes and gametocytes and by immunoprecipitation. Selected hybridomas were enriched for antigen-specific cells by stepwise cloning procedure ($1 \times 10^4$ to 10 cells per well). Enriched cells were cloned by limiting dilution at 0.25 cell/well at least twice, expanded in culture and injected i.p. into 'Pristane'-primed CAF1 mice for ascitic fluid production. For isotype analysis, Immulon-2 plates were coated with 100 ng/well of purified class-specific heavy chain reagents (rabbit anti-mouse IgM, IgG1, IgG2a, IgG2b, IgG3, and IgA). After blocking with PBS-0.05% Tween-20—1% BSA, culture supernatants were added and developed with peroxidase-conjugated goat anti-mouse Ig(A,G,M) using o-phenylenediamine as the substrate. Absorbance was read at 450 nm (Molecular Device Vmax ELISA plate reader).

Radiolabeling and Processing of Parasite Antigens for Immunoprecipitation and SDS-PAGE Live gametes were radio-iodinated by lactoperoxidase-catalyzed iodination (14). Labeled parasites were extracted in Triton X-100 for immunoprecipitation (10) and SDS-PAGE analysis (15). To reduce proteins prior to immunoprecipitation, Triton X-100 solubilized parasite proteins were denatured in the presence of guanidine hydrochloride (6M final concentration). Reduction was carried out for 1 hr in the presence of 25 mM dithiothreitol followed by alkylation (50 mM iodoacetamide), to prevent reoxidation of —SH groups, for 1 hr at room temperature in the dark. Denaturation of proteins was necessary for reduction of antigens. Treated extracts were dialyzed for ≧24 hours at 4° C. against 2–3 changes of the buffer containing 10 mM Tris, 150 mM NaCl, 1 mM EDTA, 0.1% Triton X-100, 2 mM phenylmethyl sulfonyl fluoride and 0.02% NAN$_3$. Gametocyte proteins were also labeled during biosynthesis as described (10). Parasites were washed three times in leucine-free RPMI-1640 for labeling with [$^3$H]leucine and with methionine-free RPMI-1640 for labeling with Trans[$^{35}$S] label. Labeled proteins were solubilized with Triton X-100 for immunoprecipitation as above (10).

Purification of Antigens

Radio-iodinated gametes were extracted in Triton X-114 and subjected to 5 cycles of phase separation as described (16). The 230 kDa protein is recovered in the aqueous phase and the 48/45 kDa proteins in the detergent phase after phase separation. Each phase was treated to reduce proteins as described above. The aqueous phase after treatment was used as a source of reduced 230 kDa protein and the detergent phase was used for the purification of reduced 48/45 kDa antigens by electro-elution after SDS-PAGE. To purify the 27 kDa protein, Triton X-100 extract after treatment to reduce proteins was subjected to SDS-PAGE and the protein purified by electro-elution.

Measurement of Infectivity of Gametocytes in the Mosquitoes

Freshly drawn and washed human red blood cells, normal human serum, and MAbs were mixed in 1.5 ml Eppendorf tubes and warmed at 37° C. Cultures of mature gametocytes were centrifuged in prewarmed tubes at 1200 rpm for 2 minutes resuspended to 50% hematocrit in heat inactivated normal human serum (56° C., 30 min) and added to tubes containing MAbs mixture so as to yield a final hematocrit of 55%, and 1:6 to 1:10 dilution of culture in 1.0 ml total volume. Each suspension was fed to a cage containing approximately 75 female *Anopheles gambiae* G3 mosquitoes (starved for 8–10 hrs.) through a 'Baudruche' membrane using the membrane feeder maintained at 39° C. Mosquitoes were allowed to engorge for 15 min. All unfed mosquitoes were removed and the remainder maintained at 26° C. and 70% relative humidity. Eight to ten days after feeding, mosquitoes were dissected and their midguts examined for the presence of oocysts (product of sexual reproduction of parasites in the midgut).

Epitope Mapping by One-site and Two-site ELISA

MAbs were purified from ascites by FPLC using a 'protein-A Superose 10/2' column and biotinylated at a ratio of 250 μg sulfo-NHS-biotin per mg of MAb (17). Wells of Immulon-2 plates were coated overnight at 4° C. with 1×10$^5$ gametes per well (sonicated in 50 mM sodium carbonate/sodium bicarbonate, pH 9.6, and spun at 100,000 xg) and blocked in PBS-0.05% Tween-20-1% BSA for 1–2 hours at 37° C. Plates were incubated with antibodies for 2 hours at 37° C. and developed using peroxidase-conjugated Extravidin and o-phenylenediamine as the substrate. Absorbance was recorded at 450 nm. For two-site ELISA, wells were coated with 2.5 and 5 μg/ml MAb 6B6, blocked and incubated with Triton X-100 extract of gametes (1×10$^5$/well). It was then followed by incubation with biotinylated 6B6 and developed using peroxidase conjugated Extravidin.

EXAMPLE 1

Monoclonal Antibodies

Initially to search for reduction-insensitive epitopes in *P. falciparum* TBI target antigens, an attempt was made to bias the immune response in mice by immunization with gametes that had been treated with 50 mM dithiothreitol for five minutes at 95° C. to denature and reduce proteins. Only one out of a total of 371 hybrids (five fusions) obtained produced antibodies recognizing reduced forms of antigens (the 230, 48 and 45 kDa antigens of male and female gamete surface antigens upon reduction migrate in SDS-PAGE with apparent molecular weights of 260, 59 and 53 kDa). It appears that this low frequency of positive hybridomas is due to poor immunogenicity of antigens rendered by the treatment.

Another group of mice immunized at the same time with intact untreated purified gametes, however, yielded nine out of a total of 337 hybrids (five fusions) positive for the reduced forms of target antigens.

EXAMPLE 2

Recognition of Continuous and Shared Epitopes

Five clones designated as 6B6, 16C3 and 19F1 (all of IgG2b isotype), 5G3 (IgG 3) and 11G12 (IgG1), all of which produced antibodies that recognized reduced antigens, were selected for further study. All the MAbs recognized only the reduced form of 230 and 48/45 kDa gamete surface antigens in immunoprecipitation analysis (FIG. 1 lanes 2) and failed to recognize any of these antigens in non-reduced form (lanes 1). In addition, four MAbs 6B6, 11G12, 16C3 and 19F1 also immunoprecipitated, from both non-reduced and reduced antigens preparations, a protein migrating in the 25–30 kDa (27 kDa) region of the gel. Parasites antigens in the extracts reduced after denaturation in the presence of 6M guanidine-HCl or 8M urea or triethylamine pH 11.5 all showed identical reactivity patterns with MAbs. To rule out the possibility that co-immunoprecipitation of different antigens is not due to aggregation of antigens by the conditions of denaturation and reduction, each protein was purified and then retested in immunoprecipitation analysis. The immunoprecipitation results in FIG. 2 clearly show that purified antigens were independently immunoprecipitated by the MAbs. Hence these MAbs recognize epitopes shared among various sexual stage antigens.

Two shared continuous epitopes were identified. An epitope (I) recognized by the MAb 5G3 is shared between the 230 and the 48/45 kDa gamete surface antigens. The other epitope (II) (designated as C$^3$-epitope), recognized by MAbs 6B6, 11G12, 16C3 and 19F1, is shared among the gamete surface antigens (Mr 230, 48, 45 kDa) as well as a 27 kDa antigen.

Further experiments were undertaken to characterize the Mr 27 kDa protein, as two totally unrelated proteins in this Mr range are present in the sexual stages of *P. falciparum*. One of them is the 25 kDa protein, another target of TBI, produced after initiation of gametogenesis and fertilization in the mosquito midgut (7–9,11,12) and the other one is a highly abundant (≧5%) internal protein of Mr 27 kDa produced soon after sexual commitment of parasites and continuing through gametocyte development and maturation in the vertebrate host (18,19).

Figure 3A:
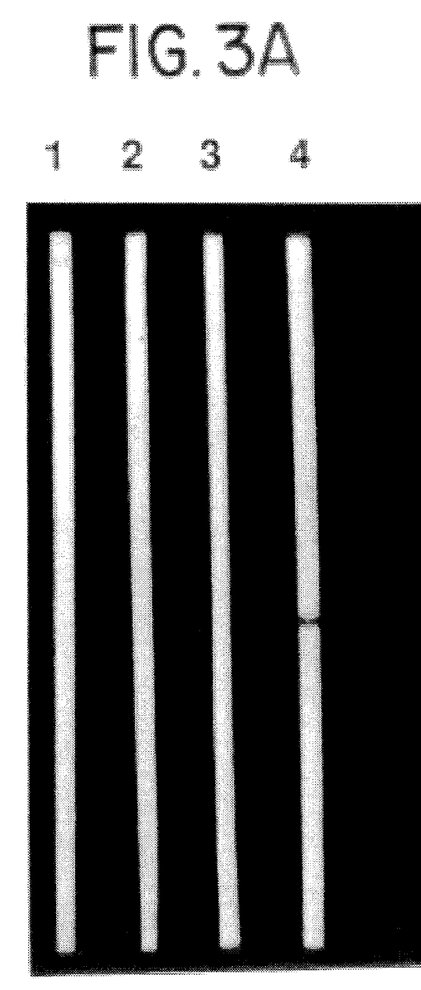
FIG. 3 is an immunoblot analysis characterizing the low Mr (~27 kDa) protein.
Figure 3B:
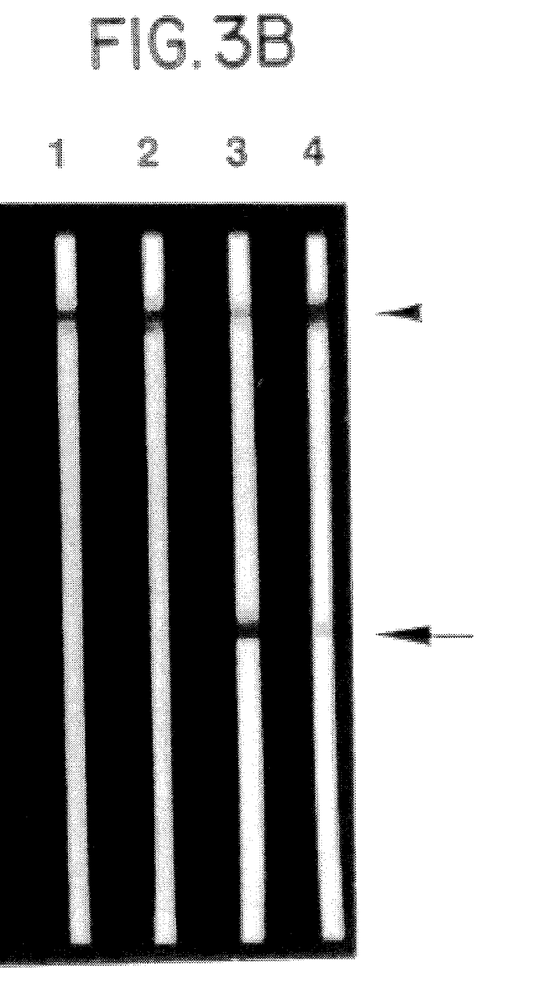

Proteins in Triton X-100 extracts of gametocytes were immunoprecipitated using MAbs 1H12 and 6B6. Immunoprecipitated proteins were fractionated by 12.5% SDS-PAGE under non-reducing conditions and transferred onto nitrocellulose membranes. Strips of nitrocellulose membranes were then reprobed for immunoreactivity with various MAbs. A MAb 1C7 directed against the 25 kDa protein failed to react with the 27 kDa protein recognized by the $C^3$-epitope MAb 6B6 (FIG. 3, panel B lane 2). Also as shown in FIG. 5, the 27 kDa protein identified by the MAb 6B6 is synthesized in the gametocytes in contrast to the 25 kDa protein which is expressed by the parasites only in the mosquito midgut (11,12).

MAbs 1H12 and 4B2, directed against the gametocyte 27 kDa protein (18,19) were likewise tested. As shown in FIG. 3, the protein immunoprecipitated by MAb 1H12 was specifically recognized by MAb 6B6 (lanes 3 and 4 in panel A). Likewise, protein immunoprecipitated by 6B6 was recognized by MAbs 4B2 and 1H12 (lanes 3 and 4 in panel B). Proteins immunoprecipitated by MAbs 1H12 and 6B6 were also purified by electroelution from SDS-PAGE, labeled by radio-iodination by the 'Iodogen' method (20) and retested in immunoprecipitation with various MAbs. The 27 kDa protein purified by 1H12 reacted with the MAb 6B 6 in immunoprecipitation and vice versa.

Figure 1:
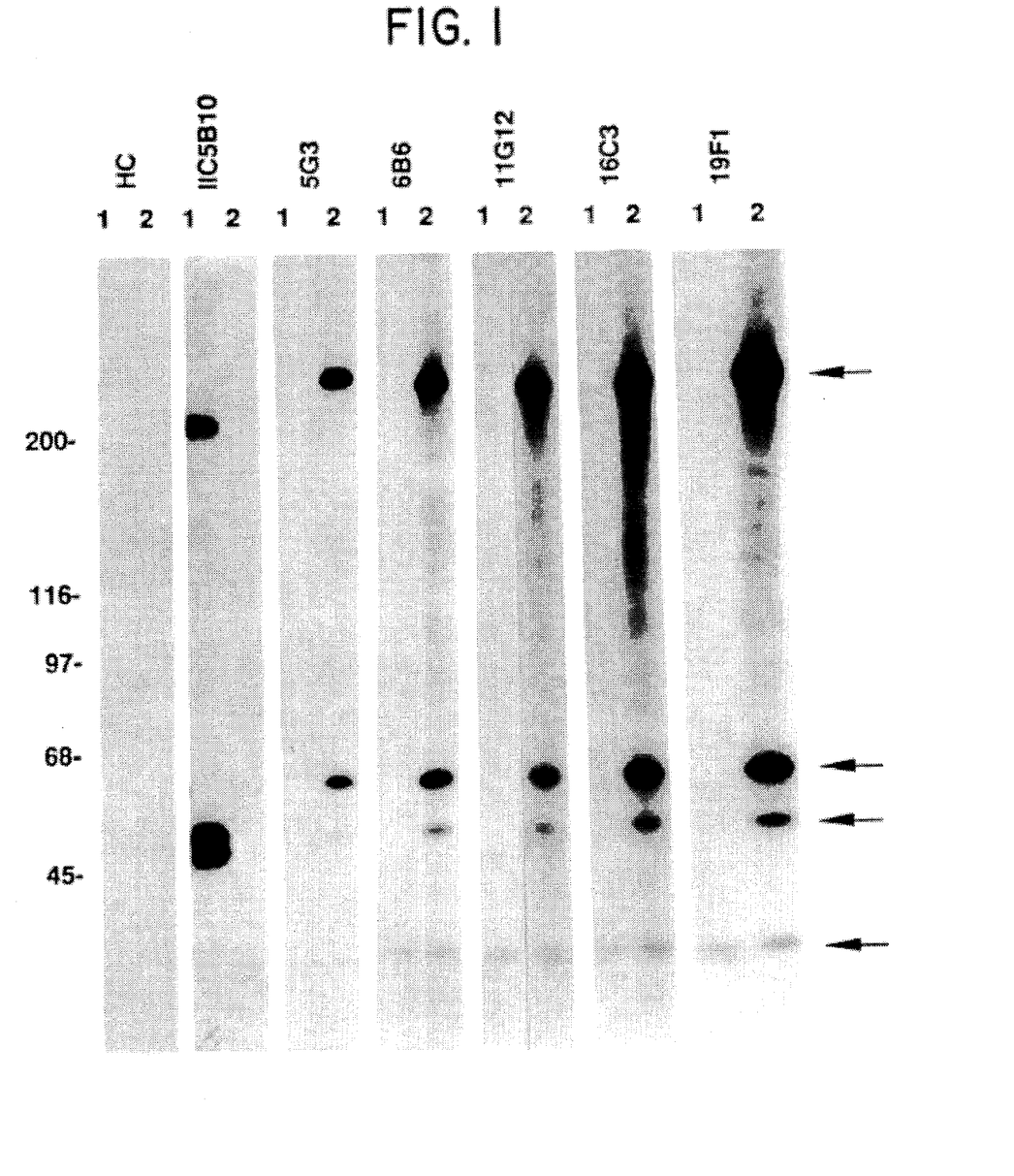
FIG. 1 illustrates the immunoprecipitation of *P. falciparum* gamete antigens by MAbs.
Figure 2A:
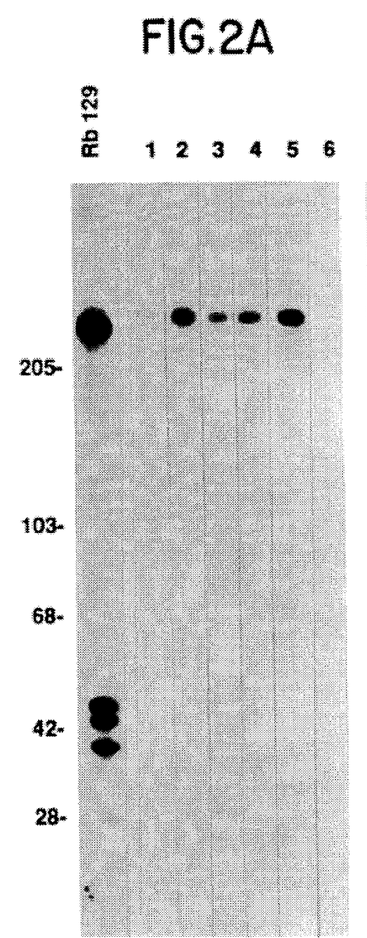
FIG. 2 provides a demonstration of cross-reacting continuous epitopes in antigens by immunoprecipitation.
Figure 2B:
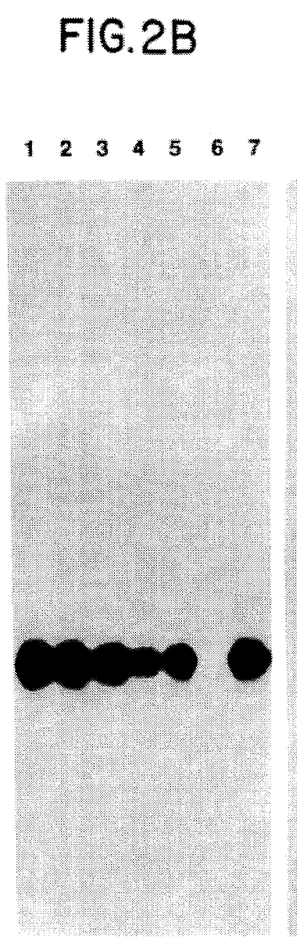
Figure 2C:
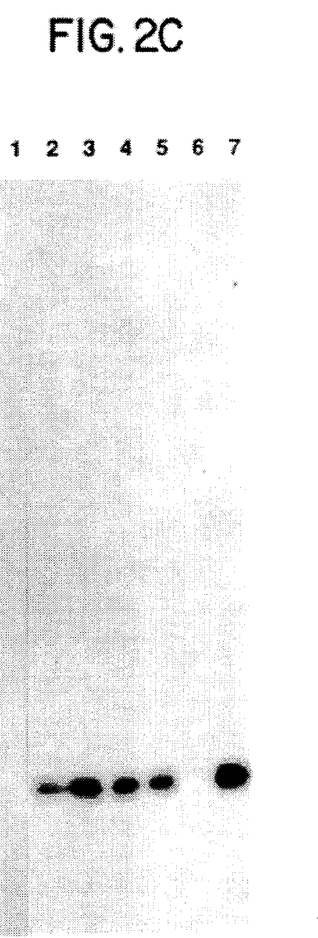

The foregoing establishes that the 27 kDa protein recognized by MAbs described here is immunologically similar to the 27 kDa protein present in the gametocytes and gametes and not the zygote/ookinete 25 kDa antigen. Iodination of the 27 kDa protein as shown in FIGS. 1 and 2 is most likely due to labeling of the 27 kDa abundant internal protein, during surface radio-iodination of gametes.

The hybridomas which produced monoclonal antibodies 6B6, 16C3, 19F1, 5G3, and 11G12 were deposited with the American Type Culture Collection, 12301 Parklawn Drive, Rockville, Md. 20852 on Oct. 14, 1992. The respective deposit numbers are HB11155, HB11158, HB 11157, HB 11156, and HB11154.

EXAMPLE 3

Blocking of Infectivity of Gametocytes to Mosquitoes

In membrane feeding experiments, MAbs recognizing $C^3$-epitope significantly blocked the infectivity of gametocytes in A. gambiae mosquitoes. The MAbs reduced the rate of infection (percent of mosquitoes infected) as well as numbers of oocysts per mosquito when compared to control MAb in parallel tests. The ability of $C^3$-epitope MAbs to block infectivity of gametocytes was not dependent on the presence of complement (Table I). MAb 5G3, on the other hand, which recognizes the epitope I did not affect the infectivity of P. falciparum gametocyte in the mosquitoes. Differences in the level of blocking between the four MAbs recognizing $C^3$-epitope could be due to differences in the amounts of immunoglobulins present in the ascitic fluid or due to differences in the affinities of MAbs of different isotypes. Protein-A purified MAb 6B6, when tested in feeding experiments, produced nearly 100% blocking in the presence of 250 µg/ml, ~ 85% blocking at 100 µg/ml and ~20% blocking at 10 µg/ml, results similar to those reported for MAbs directed against conformational epitopes in the 230 kDa protein (6).

TABLE I

Effect of MAbs on infectivity of P. falciparum gametocytes in A. gambiae

| MAb* | No. of oocysts‡ | (Infected/Dissected)σ Native | Percent Reduction‖ | No. of oocysts‡ | (Infected/Dissected)σ Heat inactivated† | Percent Reduction‖ |
|---|---|---|---|---|---|---|
| Control | 5.7 | (80/98) | 99.8 | 52.1 | (36/45) | 94.0 |
| 6B6 | 0.01 | (2/104) |  | 3.1 | (23/42) |  |
| Control | 6.9 | (89/111) | 78.3 | 10.3 | (55/75) | 74.8 |
| 11G12 | 1.5 | (50/95) |  | 2.6 | (38/75) |  |
| Control | 3.1 | (107/173) | 77.4 | 9.5 | (76/98) | 80.0 |
| 16C3 | 0.7 | (44/161) |  | 1.9 | (50/95) |  |
| Control | 14.2 | (83/96) | 85.2 | 10.3 | (55/75) | 70.9 |
| 19F1 | 2.1 | (42/80) |  | 3.0 | (47/75) |  |
| Control | 4.7 | (87/135) | 29.8 | 7.0 | (85/103) | 2.8 |
| 5G3 | 3.3 | (69/120) |  | 6.8 | (65/90) |  |

*Ascites containing control and test MAbs were tested at 1:4 dilution in membrane feeding experiments.
†Ascites fluids were heat inactivated by incubation at 56° C. for 45 min.
‡Average (2 to 6 independent infective feeds) of geometric means of total number of oocysts per mosquito.
σTotal number of mosquitoes infected/total number of mosquitoes dissected.
‖Percent reduction in the number of oocysts compared to controls. The differences between controls and MAbs (6B6, 11G12, 16C3 and 19F1) are statistically significant as revealed by $x^2$ analysis (Rate of infection, $P < 0.05$ to $P < 0.0001$; number of oocysts/mosquito, $P < 0.05$ to $P < 0.001$) (Statistic PC DOS Version 2.0).

The $C^3$-epitope MAbs (strongly IFA positive with methanol-fixed gametes and gametocytes) showed no evidence for surface reactivity when tested with intact live gametes. The mechanism of blocking thus remains unexplained. It has been found that a ~40% reduction occurs in the number of ookinetes (stages produced within 20–24 hours by the transforming zygotes) in the 6B6 fed mosquitoes. Any ookinetes present in the MAb fed mosquitoes were retarded in their growth or morphologically deformed and failed to develop into oocysts. MAbs when fed 4 days after the infectious blood meal (earliest time point when mosquitoes could take the second blood meal) had no effect on the outcome of infection in the mosquitoes. Thus blocking MAbs appear to act on the parasite within the first 24 hours of the blood meal. It is possible that during exflagellation/gametogenesis and fertilization of parasites in the mosquito midgut (21–24), the target continuous epitope present in the gamete surface antigens and in the internal 27 kDa protein might be transiently exposed and thus recognized by antibodies.

EXAMPLE 4

Epitope Mapping

Figure 4:
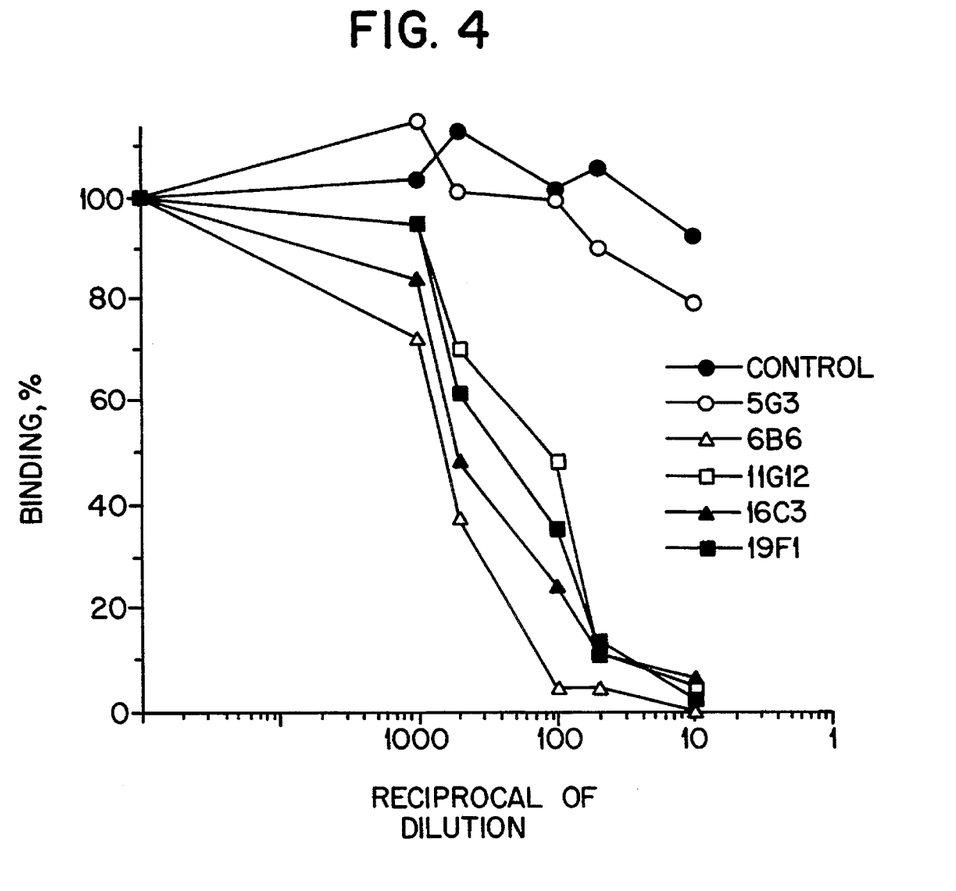
FIG. 4 shows epitope analysis by one-site ELISA.

A one site ELISA was performed to delineate the epitopes recognized by transmission blocking and non-blocking MAbs. As shown in FIG. 4, all the four transmission-blocking MAbs 6B6, 11G12, 16C3 and 19F1 which exhibited identical immunoreactivity patterns, appear to recognize the same or very closely linked epitope(s). Two-site ELISA also suggested that this epitope is not repeated in the antigens. As expected, MAb 5G3, which shows a different immunoreactivity pattern and does not block transmission, also did not compete for binding with biotinylated 6B6. These MAbs thus recognize two continuous and cross-reacting epitopes (I and $C^3$) of which $C^3$-epitope is a potent target of transmission blocking antibodies.

EXAMPLE 5

Conservation of $C^3$-epitope

Figure 5A:
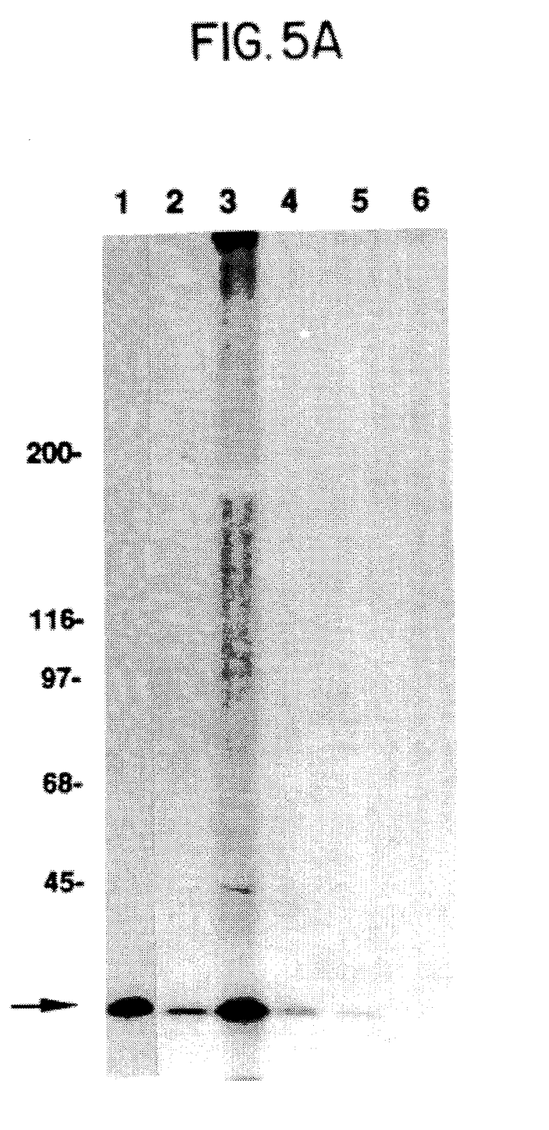
FIG. 5A demonstrates the reactivity of MAb 6B6 with antigens in *P. falciparum* isolates of various geographic locations. Gametocytes of *P. falciparum* clones 3D7 were labeled with Tran$^{35}$S-label (lane 1) and others: T4 (lane 2), LES (lane 3), ItD12 (lane 4), and 7G8 (lane 5) were labeled with leucine. Labeled parasites were extracted with Triton X-100 and used for immunoprecipitation with MAb. Lane 6 shows immunoprecipitation of T4 parasite extract with an unrelated MAb.
Figure 5B:
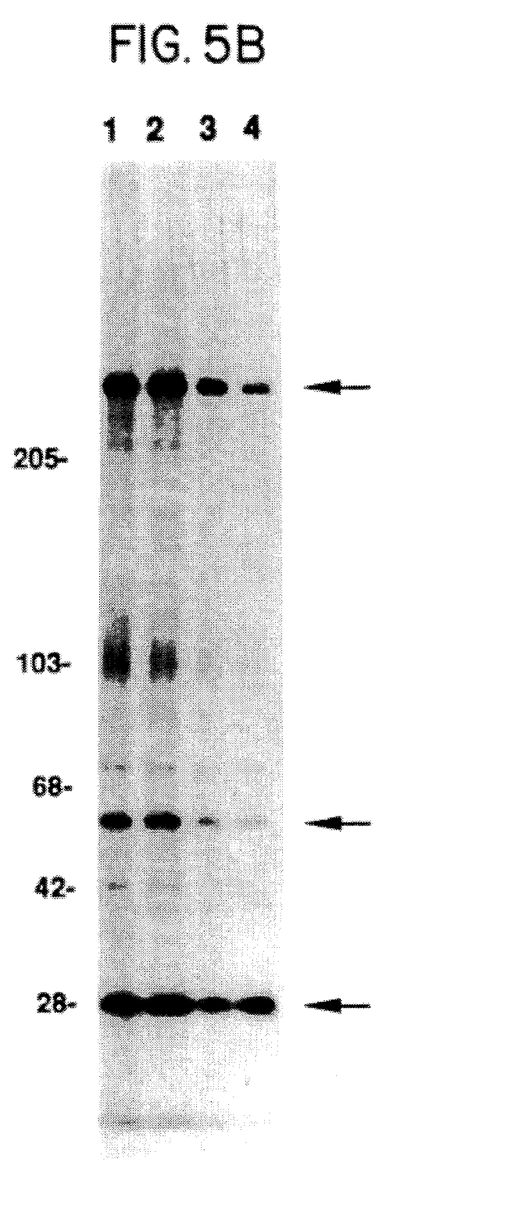
FIG. 5B also demonstrates the reactivity of MAb 6B6 with antigens in *P. falciparum* isolates of various geographic locations. Triton X-100 extracts of surface radioiodinated gametes of 7G8 (lane 2), T4 (lane 3), and 3D7 (lane 4) were denatured, reduced, and alkylated as described before immunoprecipitation with MAb 6B6. Lane 1 shows immunoprecipitation of 3D7 parasite extract with rabbit antigamete serum. The samples were analyzed by 5–15% SDS/PAGE under nonreducing conditions.

The blocking epitope recognized by MAb 6B6 appears conserved in parasites from diverse geographical locations. A 27 kDa protein was immunoprecipitated by MAb 6B6 from biosynthetically labeled gametocytes from *P. falciparum* clones 3D7, T4, LE5, ItD12, and 7G8 (FIG. 5A). In other experiments, MAb 6B6 immunoprecipitated reduced forms of 230 kDa, 48/45 kDa, and the 27 kDa proteins from the extracts of surface radio-iodinated gametes of 7G8, T4, and 3D7 parasites (FIG. 5B).

To detect MAb-6B6 epitope-specific antibodies in human sera, a radioimmunoassay (RIA) was developed. Radio-iodinated r-27 kDa protein was pre-incubated with various dilutions of human sera and then added to RIA plates coated with protein A purified MAb-6B6. The presence of epitope-specific antibodies is indicated by a reduction in the counts (percent binding). Results of 56 sera from Thailand which were analyzed (FIG. 6), demonstrate that the linear epitope ($C^3$) is a target of immune response during natural infection.

EXAMPLE 6

Expression of the Gene for the 27 kDa Antigen and Mapping of $C^3$-epitope

Figure 7:
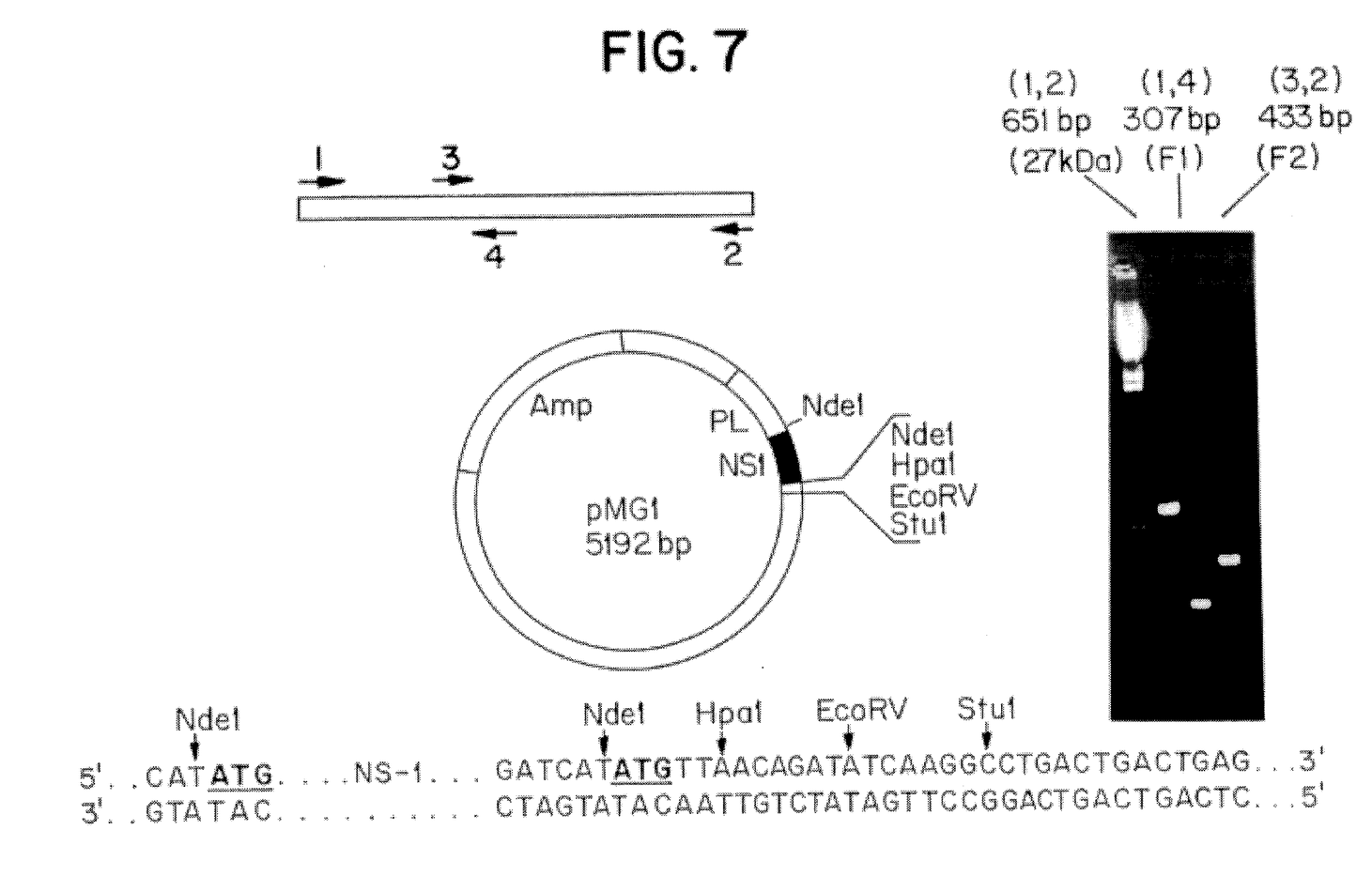
FIG. 7 illustrates the PCR cloning/expression in pMG1 referred to in Example 6.

The entire coding sequence for the 27 kDa protein was amplified by polymerase chain reaction (PCR) using synthetic oligonucleotides (oligs 1 and 2). Two overlapping DNA fragments were likewise obtained by PCR using pairs of oligos 1 and 4 (designated as F1) and oligos 3 and 2 (F2) by PCR (FIG. 7). The PCR DNA products, single major bands, were purified, treated with T4 DNA polymerass and ligated to pMG1 in the EcoRV site for the full length and F1, and in the Hpal site for the F2 fragment (SEQ ID NO:2). Ligated DNA was first used for transformation of *E. coli* MM294 CI+. Positive transformants were identified by hybridization with the end labeled-oligonucleotide #3. Orientation of the insert was identified by PCR using an oligo from the pMG1 sequence and either oligo 2 or oligo 4. DNA from representative clones were sequenced to verify the reading frame and also to ensure that the PCR products have the same sequence as the original clone.

Figure 8:
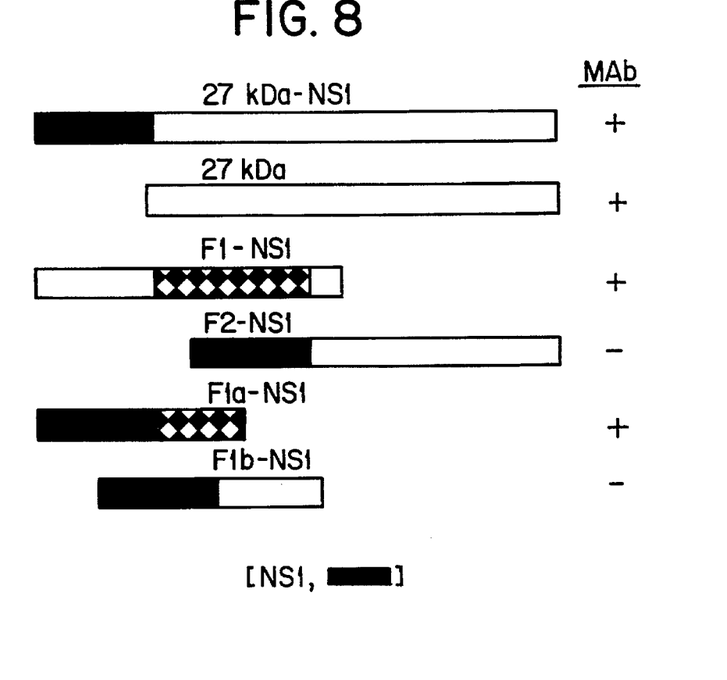
FIG. 8 graphically shows the immunoreactivity of transmission blocking MAbs to the recombinant 27 kDa antigen and overlapping fragments. As shown, the epitope recognized by MAb 6B6 was centered in the F1a sub-fragment.

DNA from appropriate clones was then used to transform *E. coli* AR58 for expression. After confirming expression, the NS1 sequence was deleted by NdeI digestion to express clones without NS1 sequences. Expressed products were analyzed by 15% SDS-PAGE, transferred onto nitrocellulose membrane and probed with the MAb. As shown in FIG. 8, the epitope recognized by transmission-blocking MAb 6B6 was localized in the Fragment F1.

In order to localize the blocking epitope more accurately, oligonucleotide primers were designed to obtain two overlapping sub-fragments of the immuno-reactive F1 fragment of the 27 kDa protein. The PCR products were likewise cloned in pMG1 and expressed products probed on Western blots using the MAb 6B6. As shown in FIG. 8, the amino-terminal sub-fragment F1a was recognized by MAbs.

A method for immuno-affinity purification of r-27 kDa protein from the soluble fraction of bacterial lysates has also been developed. The antibody column was constructed by chemically cross linking antibody to protein A-Sepharose beads using dimethyl suberimidate. It was found that triethylamine (pH 11.5) is the most effective eluant without causing any apparent damage to the antibody column. The yield of r-27 kDa protein purified from the column was in the order of 3–5 mg/liter of *E. coli* culture. Purified proteins will greatly facilitate various aspects of T cell work including identification T helper epitope.

Figure 9:
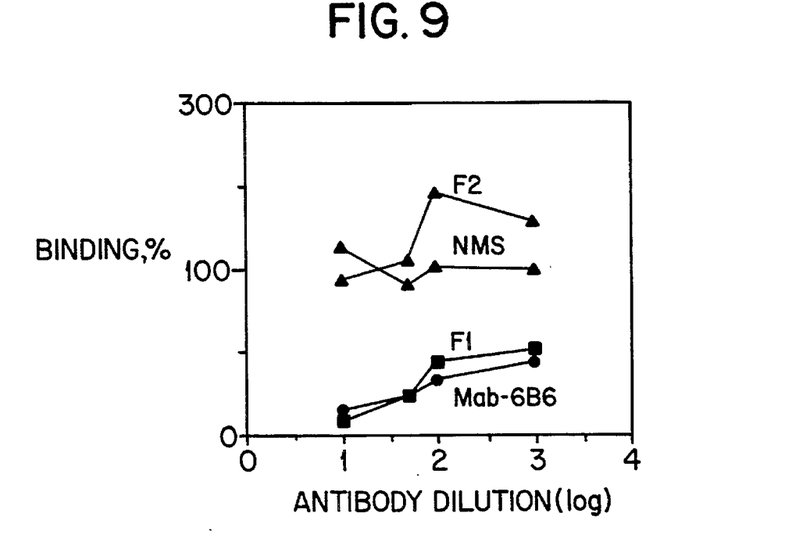
FIG. 9 graphically shows the induction of antibodies (6B 6epitope specific) in mice using the r-F1 fragment.

It is contemplated that immunization with recombinant proteins according to the invention will elicit antibodies that, 1) are capable of recognizing antigen in the parasites, 2) will recognize the same epitope recognized by the MAbs and 3) will reduce infectivity of gametocytes in the mosquitoes. Mice have been immunized with purified F1 and F2 fragments and sera analyzed in a competitive ELISA for antibodies against the epitope recognized by MAbs and also in membrane feeding studies for blocking of infection in the mosquitoes. FIG. 9 shows that immunization with r-F1 does induce antibodies against the epitope recognized by the MAb-6B6. As expected, anti-F2 and normal mouse sera did not compete for binding to MAb-6B6 epitope. In membrane feeding experiments (Table II), pooled anti-F1 serum also caused approximately 80% inhibition of infectivity of gametocytes in the mosquitoes. Once again, anti-F2 sera did not inhibit infectivity of gametocytes.

TABLE II

Induction of Transmission-Blocking Antibodies In Mice By r-F1 Fragment of 27 kDa Antigen

| Ab | Rate of Infection* | # Oocyst |
|---|---|---|
| NMS | 48 | 3.6 |
| Mab-686 | 0 | 0 |
| anti-F1 | 20 | 0.8 |
| anti-f2 | 40 | 4.0 |

*Positive/Total dissected.

EXAMPLE 7

Based on the amino acid sequence of the immunoreactive F1a sub-fragment, synthetic peptides (20 amino acids long) were employed to precisely map the $C^3$ epitope. A peptide (SEQ ID NO:1) having the following sequence was identified by the MAbs:

Met—Ser—Lys—Val—Gln—Lys—Asp—Ser—Ala—

—Lys—Pro—Leu—Asp—Lys—Phe—Gly—Asn—

—Ile—Tyr—Asp

Using a single letter code, the sequence of the peptide epitope (SEQ ID NO:1) is

M-S-K-V-Q-K-D-S-A-K-P-L-D-K-F-G-N-I -Y-D

While the drawings have been referred to above, the following more detailed discussion regarding each figure may be useful to a better understanding of the invention:

FIG. 1 relates to immunoprecipitation of *P. falciparum* gamete antigens by MAbs, Purified live gametes were radio-iodinated with $^{125}$I and Triton X-100 extracts were treated to denature/reduce and alkylate proteins as described in the Examples.

Untreated (lanes 1) and treated (lanes 2) extracts were immunoprecipitated with various MAbs (indicated on top of each pair of two lanes) and analyzed by 5–15% SDS-PAGE under non-reducing condition. HC is an unrelated MAb used as a negative control and IIC5B10 is a MAb that recognizes a reduction-sensitive epitope in the 48/45 kDa antigens (4) and immunoprecipitates the 230kDa and 48/45 kDa antigens since they exist as a stable membrane bound complex (30). Positions of reduced antigens immunoprecipitated by MAbs are identified by arrows. High molecular weight markers were used to calibrate the gels.

FIG. 2 provides a demonstration of cross-reacting continuous epitopes in antigens by immunoprecipitation. Separate antigen preparations containing reduced –230 kDa (panel A), –48/45 (panel B) and –27 kDa (panel C) prepared as described in the Examples were analyzed by 5–15% SDS-PAGE under non-reducing conditions. Immunoprecipitations were done with MAbs 5G3 (lanes 1), 6B6 (lanes 2), 11G12 (lanes 3), 16C3 (lanes 4), 19F1 (lanes 5), a negative control MAb (lanes 6), and rabbit 129 (anti-*P. falciparum* gamete serum) (lanes 7 in panel B and C). Lane marked Rb 129 shows immunoprecipitation of non-reduced antigens from Triton X-100 extracts of radio-iodinated gametes. Molecular weight standards used were prestained high molecular weight markers.

FIG. 3 relates to the immunoblot analysis to characterize the low Mr (~27 kDa) protein. Triton X-100 extracts of purified *P. falciparum* gametocytes (3.5×10$^7$) were immunoprecipitated with MAbs 1H 12 or 6B6, proteins were separated by 12.5% SDS-PAGE under non-reducing conditions and transferred onto nitro-cellulose membranes. (A) Immunoblot of the 27 kDa antigen immunopurified with the MAb 1H12. Strips of membrane were probed with non-biotinylated negative control MAb (lane 1), biotinylated MAb 14H10 (recognizes a conformational epitope in the 230 kDa antigen), and biotinylated MAb 6B6 in the presence (lane 3) or absence (lane 4) of 100-fold excess of non-biotinylated 6B6. All the strips were treated with 1:3000 dilution of Extravidin-peroxidase and developed using diaminobenzidine as the substrate. (B) Immunoblot of the 27 kDa antigen immunopurified with the MAb 6B6. Stripes were probed with no antibody (lane 1), MAb 1C7 (lane 2), MAb 4B2 (lane 3), and MAb 1H12 (lane 4). All the strips were treated with 1:1000 dilution of peroxidase conjugated goat anti-mouse immunoglobulins (A, G, M) and developed using diaminobenzidine as the substrate. The 27 kDa protein is indicated by an arrow. The band on top (arrowhead) in panel B is due to reactivity of conjugate to mouse immunoglobulins in the immunoprecipitates.

FIG. 4 relates to the epitope analysis by one-site ELISA. Various competing ascites were tested at final dilutions ranging from 1:10 to 1:1000 and the fixed optimum concentration (5 μg/ml) of biotinylated MAb 6B6.

FIG. 5 reactivity of mAb 6B6 with antigens in *P. falciparum* isolates of various geographic locations. (A) Gametocytes of *P. falciparum* clones 3D7 were labeled with Tran$^{35}$S-label (lane 1) and others; T4 (lane 2), LES (lane 3), ItD12 (lane 4), and 7G8 (lane 5) were labeled with [$^3$H] leucine. Labeled parasites were extracted in Triton X-100 and used for immunoprecipitation with MAb 6B6, Lane 6 shows immunoprecipitation of T4 parasite extract with an unrelated MAb. (B) Triton X-100 extracts of surface radio-iodinated gametes of 7G8 (lane 2), T4 (lane 3), and 3D7 (lane 4) were denatured, reduced, and alkylated as described before immunoprecipitation with MAb 6B6. Lane 1 shows immunopreciparation of 3D7 parasite extract with rabbit anti-gamete serum. The samples were analyzed by 5–15% SDS/PAGE under nonreducing condition. Molecular weight standards used to calibrate the gel were high molecular weight (A) and prestained high molecular weight (B).

Figure 6:
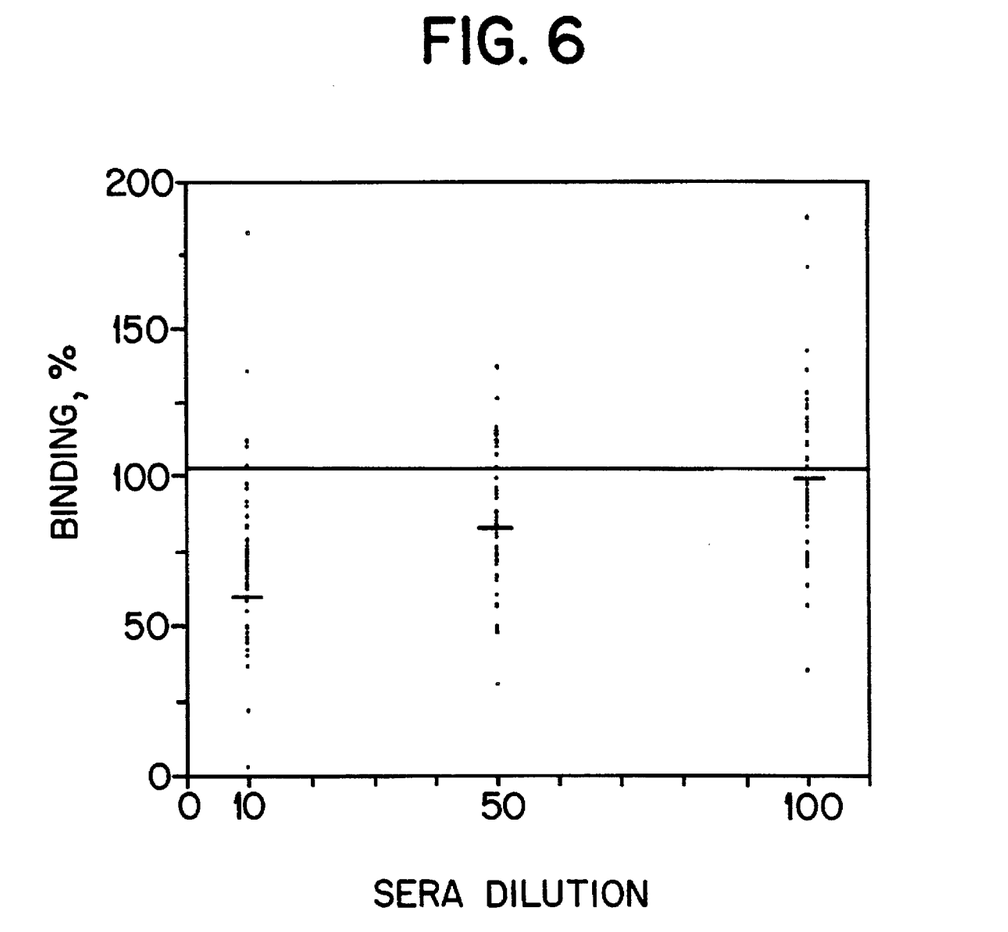
FIG. 6 graphically illustrates percent binding versus sera dilution showing antibody response against the $C^3$-epitope using sera from Thailand for test purposes.

FIG. 6 graphically illustrates percent binding versus sera dilution showing antibody response against the C$^3$-epitope using sera from Thailand for test purposes.

FIG. 7 illustrates the PCR cloning/expression in pMG1 referred to in Example 6.

FIG. 8 graphically shows the immunoreactivity of transmission blocking MAbs to the recombinant 27 kDa antigen and overlapping fragments. As shown, the epitope recognized by MAb 6B6 was centered in the F1a sub-fragment.

FIG. 9 graphically shows the induction of antibodies (6B6-epitope specific) in mice using the r-F1 fragment.

Aspects of the foregoing may be further summarized or described as follows: Antigens in the sexual stages of malaria parasite have been identified in the past using monoclonal antibodies (MAbs) as the targets of malaria transmission blocking immunity (3). These MAbs act either before or after fertilization of gametes and result in the reduction of infectivity of gametocytes in the mosquitoes. In *P. falciparum*, three proteins (apparent molecular weights 230, 48 and 45 kDa) on the surface of gametes and a protein designated as Pfs25 (25 kDa) present on the surface of zygotes undergoing transformation into ookinetes have previously been identified as the target antigens.

In most cases, epitopes recognized by such MAbs are reduction-sensitive (conformational) and thus pose real difficulties for cloning genes from prokaryotic expression libraries. The reduction-sensitivity of such epitopes also makes them less attractive candidates for any synthetic vaccine development. In contrast, the present invention uses MAbs which recognize continuous (reduction-insensitive) epitopes thereby overcoming or minimizing prior art problems.

According to the invention, MAbs recognizing continuous epitopes were obtained as follows:

A total of 708 hybridomas cell lines were obtained from ten fusions. Hybridoma culture supernatants were screened by IFA using air-dried and methanol fixed parasites (gametocyte and gametes) followed by immunoprecipitation using detergent extracts of radioiodinated gametes. Several dozens of MAbs directed against conformational epitopes were thus obtained. To identify MAbs recognizing continuous (linear) epitopes, proteins in the extract were reduced and alkylated (denatured/reduced/alkylated; D/R/A antigen) prior to immunoprecipitation. Initially ten hybrids from five independent fusions tested positive by immunoprecipitation using D/R/A antigen. Further cloning of positive hybridomas produced five MAbs recognizing D/R/A antigens. MAbs 6B6, 16C3 and 19F1 were isotyped as IgG2b and MAbs 5G3 and 11G12 were of IgG3 and IgG1 isotype, respectively. Immunoprecipitation using D/R/A antigen extract revealed that MAb 5G3 recognizes linear epitopes shared between the 230 kDa and the 48/45 kDa doublet gamete surface antigens.

The remaining four MAbs immunoprecipitated a protein of 27 kDa from detergent extracts of radioiodinated gametes or biosynthetically labeled gametocytes. In addition, they also recognized a linear epitope shared among the 230, 48/45 kDa and the 27 kDa protein. The immunological cross-reactivity between various antigens was further confirmed by using D/R/A forms of individually purified (either by electro-elution or by Triton X-114 phase separation) for immunoprecipitation. All five MAbs also reacted with fixed parasites in IFA but failed to give any positive reactivity in IFA using live gametes.

Epitope analysis included the following:

A one site ELISA was employed to determined the epitope specificity of all the five MAbs recognizing linear epitopes shared between various antigens. MAbs 6B6 and 16C3 were biotinylated and tested in a competitive ELISA using plates coated with the extract of sonicated gametes. Two cross-reacting linear epitopes were identified. One such epitope recognized by the MAb 5G3 is shared between the 230 kDa and the 48/45 kDa proteins. Another shared epitope was identified by other four MAbs recognizing linear epitopes in the 230, 48/45 kDa and the 27 kDa protein. One site ELISA and immunodepletion analysis using a number of human sera also suggested that the linear epitope shared among the 27 kDa antigen and the 230 and 48/45 kDa antigens is also the target of natural immune response during malaria infection.

The effect on the infectivity of gametocytes in the mosquitoes was shown as follows:

All the MAbs were tested in membrane feeding experiments using cultured *P. falciparum* (3D7 clone of NF54) gametocytes and *A. gambiae* mosquitoes. Number of oocysts and rate of infection was calculated to assess the infectivity blocking effects of MAbs. MAb 5G3 did not have any transmission blocking effect with or without complement. The other four MAbs when tested in the presence or absence of complement, produced different levels of transmission blocking effects. MAb 6B6 in particular, resulted in nearly 100% blocking even in the absence of complements (Table 1).

With respect to antigen-specific T cells, a T cell line responding predominantly to antigens in the molecular weight regions of 25–30 kDa (T cell Western blot) has been obtained from mice hyperimmunized with purified gametes. This line can be cloned to obtain antigen specific T cell clones and to produce T cell hybridomas. These antigen specific T cell clones will be useful in the identification of T cell epitopes.

It will be recognized that the invention provides MAbs recognizing linear (continuous, reduction-insensitive) epitopes in the sexual stages of *P. falciparum*. Four of these MAbs recognize a linear epitope shared among the gamete surface proteins of 230, 48/45 kDa and a protein of 27 kDa produced in the early stages of gametocytes and present also in the mature stages of gametocytes. These antibodies also block infectivity of gametocytes in the mosquitoes. A second linear epitope is shared among the 230 and the 48/45 kDa proteins only and does not appear to be a blocking epitope. Sequence identification of the target blocking epitope and relevant T cell epitope using T cell clones may be used to develop a malaria transmission blocking vaccine. The linear nature of the blocking epitope shared among several antigens which are the targets of natural immune response is an important aspect of the invention in providing a rationale for the development of a synthetic or recombinant subunit vaccine. It is contemplated that the immune response against these epitopes will be boosted by natural infection.

Vaccines according to the invention may be prepared on the basis of the continuous and cross-reacting epitope described herein using conventional knowledge of the art. The epitope may be prepared by chemical synthesis based on its amino acid sequence. Alternatively, the epitope may be obtained by expression using an appropriate cell system preferably bacterial although other systems, e.g. Chinese hamster ovary cells, yeast, bacuolo virus or live vectors may also be used.

Literature references noted above are listed below:
1. Miller, L. H., Howard, R. J., Carter, R., Good, M. F., Nussenzweig, V. & Nussenzweig, R. S. (1986) Science 234, 1349–1356.
2. Good, M. F., Kumar, S. & Miller, L. H. (1988) Immunol. Today, 9, 351–355.
3. Carter, R., Kumar, N., Quakyi, I. A., Good, M. F., Mendis, K. N., Graves, P. M. & Miller, L. H. (1988) Prog. Allergy, 41, 193–214.
4. Rener, J., Graves, P. M., Carter, R., Williams, J. L. & Burkot, T. R. (1983) J. Exp. Med. 158, 976–981.
5. Vermeulen, A. N., Ponnudurai, T., Beckers, P. J. A., Verhave, J., Smith, M. A. & Meuwissen, J. H. E. (1985) J. Exp. Med. 162, 1460–1476.
6. Quakyi, I. A., Carter, R., Rener, J., Kumar, N., Good, M. F. & Miller, L. H. (1987) J. Immunol. 139, 4213–4217.
7. Kaslow, D. C., Quakyi, I. A., Syin, C., Raum, M. G., Keister, D. B., Coligan, J. E., McCutchan, T. F. & Miller, L. H. (1988) Nature 333, 74–76.
8. Vermeulen, A. N., Deursen, J. V., Brakenhoff, R. H., Lensen, T. H. W., Ponnudurai, T. & Meuwissen, J. H. E. (1986) Mol. Biochem. Parasitol. 20, 155–163.
9. Grotendorst, C. A., Kumar, N., Carter, R. & Kaushal, D. C. (1984) Inf. Immun. 45, 775–777.
10. Kumar, N. & Carter, R. (1984) Mol. Biochem. Parasitol. 13, 333–342.
11. Kumar, N. & Carter, R. (1985) Mol. Biochem. Parasitol. 14, 127–139.
12. Fries, H. C. W., Lamers, M. B. A. C., Deursen, J. V., Ponnudurai, T. & Meuwissen, J. H. E. (1990) Exp. Parasitol. 71, 229–235.
13. Ifediba, T. & Vanderberg, J. P. (1981) Nature 296, 364–366.
14. Howard, R. J., Kaushal, D. C., & Carter, R. (1982) J. Protozool. 29, 114–117.
15. Laemmli, U. K. (1970) Nature 227, 680–685.
16. Kumar, N. (1985) Mol. Biochem. Parasitol. 17, 343–358.
17. Harlow, E. & Lane D. (1988) in Antibodies —a laboratory manual (Cold Spring Harbor Laboratory), pp. 340–341.
18. Carter, R., Graves, P. M., Creasey, A., Byrne, K., Reed, D., Aalno, P. & Fenton, B. (1989) Exp. Parasitol. 69, 140–149.
19. Bruce, M. C., Alano, P., Duthie, S. & Carter, R. (1990) Parasitology, 100, 191–200.
20. Fraker, P. J. & Speck, J. C. (1978) Biochem. Biophys. Res. Comm., 80, 849–857.
21. Nijhout, M. M. & Carter, R. (1978) Parasitology, 76, 39–53.
22. Nijhout, M. M. (1979) Exp. Parasitol., 48, 75–80.
23. Carter, R. & Nijhout, M. M. (1977) Science 195, 407–409.
24. Sniden, R. E. (1983) Adv. Parasitol. 22, 153–216.
25. Walliker, D., Quakyi, I. A., Wellems, T. E., McCutchan, T. F., Szarfman, A., London, W. T., Corcoran, L. M., Burkot, T. R. & Carter, R. (1987) Science 236, 1661–1666.
26. Graves, P. M., Carter, R., Burkot, T., Quakyi, I. A. & Kumar, N. (1988) Parasite Immunol., 10, 209–218.
27. Ong, C. S. A., Zhang, K. Y., Eida, Graves, P. M., Dow, C., Looker, M., Rogers, N. C., Choidini, P. L. & Targett, G. A. T. (1990) Parasite Immunol., 12, 447–456.
28. Carter, R., Graves, P. M., Quakyi, I. A. & Good, M. F. (1989) J. Exp. Med. 169, 135–147.
29. Quakyi, I. A., Otoo, L. N., Pombo, D., Sugars, L. Y., Menon, A., DeGroot, A. S., Johnoson, A., Alling, D., Miller, L. H. & Good, M. F. (1989) Am.J.Trop. Med. & Hyg. 41, 125–134.
30. Kumar, N. (1987) Parasite Immunol. 9, 321–335.

Having described the invention in the foregoing what is claimed as new is:

1. Monoclonal antibodies 6B6, 16C3, 19F1, or 11G12, represented by ATCC deposit numbers HB11155, HB11158, HB11157, and HB11154 respectively, which recognize a continuous epitope in the gametocyte stage of *P. falciparum* having the amino acid sequence set forth in SEQ ID NO:1, which is a shared continuous epitope among the 230, 48/45 and 27 kDa gamete surface proteins.

2. Hybridomas expressing the monoclonal antibodies according to claim 1.

3. An isolated protein having an amino acid sequence which corresponds to the continuous epitope shared among the gamete surface proteins 230 and 48/45 and 27 kDa wherein the protein consists of an epitope having the amino acid sequence set forth in SEQ ID NO:1.

* * * * *